United States Patent [19]
Fairbanks et al.

[11] Patent Number: 6,117,879
[45] Date of Patent: Sep. 12, 2000

[54] METHODS OF USING MOXONIDINE TO INHIBIT NOCICEPTIVE PAIN

[75] Inventors: Carolyn A. Fairbanks, NE. Rochester; George L. Wilcox, N. Golden Valley, both of Minn.; Laura S. Stone, E. Richmondhill, Canada; Kelley F. Kitto, Minneapolis, Minn.

[73] Assignee: Solvay Pharmaceuticals GmbH, Hannover, Germany

[21] Appl. No.: 09/152,344

[22] Filed: Sep. 14, 1998

Related U.S. Application Data

[60] Provisional application No. 60/059,048, Sep. 16, 1997.

[51] Int. Cl.$^7$ .................................................. A61K 31/505
[52] U.S. Cl. ........................................... 514/269; 514/256
[58] Field of Search ..................................... 514/256, 269

[56] References Cited

U.S. PATENT DOCUMENTS 5,447,947  9/1995  Campbell ................................. 514/392

FOREIGN PATENT DOCUMENTS

WO 92/14453  9/1992  WIPO .

OTHER PUBLICATIONS

Medline abstract AN 96059841, Urban, R. et al., Aug. 1995.
Armah, B.I., Hofferber, E. and Stenze, W. (1988) "General Pharmacology of the Novel Centrally Acting Antihypertensive Agent Moxonidine". *Arzneimittel–Forschung* 38: 1426–34.
Codd, E.E., Press, J.B. and Raffa, R.B. (1995) "Alpha 2–Adrenoceptors vs. Imidazoline Receptors: Implications for Alpha 2–Mediated Analgesia and Other Non–Cardiovascular Therapeutic Uses". [Review]. *Life Sciences* 56:63–74.
Ernsberger, P., Graves, M.E., Graff, L.M., Zakieh, N., Nguyen, P., Collins, A.L., Westbrooks, K.L. and Johnson, G.G. (1995) "$I_1$–Imidazoline Receptors: Definition, Characterization, and Transmembrane Signaling". *Annals New York Academy of Sciences* 763:22–42.
Ferry, D., Armah, B.I., Goll, A. and Glossmann, H. (1988) "Characteristics of the Binding of the Antihypertensive Agent Moxonidine to Alpha 2–Adrenoceptors in Rat Brain Membranes". *Arzneimittel–Forschung* 38:1442–5.
Hunter, J.C., Fontana, D.J., Hedley, L.R., Jasper, J.R., Lewis, R., Link, R.E., Secchi, R., Sutton, J. and Eglen, R.M. (1997) "Assessment of the Role of $\alpha_2$–Adrenoceptor Subtypes in the Antinociceptive, Sedative and Hypothermic Action of Dexmedetomidine in Transgenic Mice". *British Journal of Pharmacology* 122:1339–44.
Hylden, J.L.K. and Wilcox, G.L. (1981) "Intrathecal Substance P Elicits a Caudally–Directed Biting and Scratching Behavior in Mice". *Brain Research* 217:212–215.
Hylden, J.L.K. and Wilcox, G.L. (1983) "Pharmacological Characterization of Substance P–Induced Nociception in Mice: Modulation by Opioid and Noradrenergic Agonists at the Spinal Level". *The Journal of Pharmacology and Experimental Therapeutics* 226:398–404.

Janumpalli, S., Butler, L.S., MacMillan, L.B., Limbird, L.E. and McNamara, J.G. (1998) "A Point Mutation (D79N) of the $\alpha$2A Adrenergic Receptor Abolishes the Antiepileptogenic Action of Endogenous Norepinephrine". *Journal of Neuroscience* 18:2004–2008.

Jones, S.L. and Gebhart, G.F. (1986) "Characterization of Coeruleospinal Inhibition of the Nociceptive Tail–Flick Reflex in the Rat: Mediation by Spinal $\alpha_2$–Adrenoceptors". *Brian Research* 364:315–330.

Lakhlani, P.P., MacMillan, L.B., Guo, T.Z., McCool, B.A., Livinger, D.M., Maze, M. and Limbird, L.E. (1997) "Substitution of a Mutant $\alpha_{2A}$–Adrenergic Receptor Via Hit and Run Gene Targeting Reveals the Role of this Subtype in Sedative, Analgesic, and Anesthetic–Sparing Response in vivo". *Proceedings of the National Academy of Sciences of the United States of America* 94:9950–9955.

Mizobe, T., Maghsoudi, K., Sitwala, K., Tianzhi, G., Ou, J. and Maze, M. (1996) "Antisense Technology Reveals the $\alpha_{2A}$ Adrenoceptor to be the Subtype Mediating the Hypnotic Response to the Highly Selective Agonist, Dexmedetomidine, in the Locus Coeruleus of the Rat". *Journal of Clinical Investigation* 98:1076–80.

Monroe, P.J., Smith, D.L. and Smith, D.J. (1995) "Spinal Imidazoline Receptors do not Mediate the Antinociceptive Action of Intrathecal Clonidine in the Rat". *Annals New York Academy of Sciences* 763:497–500.

Reddy, S.V.R., Maderdrut, J.L. and Yaksh, T.L. (1980) "Spinal Cord Pharmacology of Adrenergic Agonist–Mediated Antinociception". *the Journal of Pharmacology and Experimental Therapeutics* 213:525–533.

Solomon, R.E., Brody, M.J. and Gebhart, G.F. (1989) "Pharmacological Characterization of Alpha Adrenoceptors Involved in the Antinociceptive And Cardiovascular Effects of Intrathecally Administerd Clonidine". *Journal of Pharmacology and Experimental Therapeutics* 251:27–38.

Ziegler, D., Haxhiu, M.A., Kaan, E.C., Papp, J.G. and Ernsberger, P. (1996) "Pharmacology of Moxonidine, an $I_1$–Imidazoline Receptor Agonist". *Journal of Cardiovascular Pharmacology* 27:S26–37.

Fairbanks, C.A. and Wilcox, G.L., "Imidazoline Receptor ($I_1$) Selective Agonists: Antinociceptive Profile Modulation of Morphine Antinociception, and Attenuation of the Development of Morphine Tolerance". Poster Abstract Presented at the 1996 Annual Meeting of the American Pain Society, Nov. 14, 1996.

*Primary Examiner*—William R. A. Jarvis
*Attorney, Agent, or Firm*—Evenson, McKeown, Edwards & Lenahan, P.L.L.C.

[57] ABSTRACT

Moxonidine and its physiologically compatible acid-addition salts are used for the treatment and/or prophylaxis of nociceptive pain, and in particular nociceptive acute and chronic pain.

3 Claims, 3 Drawing Sheets

METHODS OF USING MOXONIDINE TO INHIBIT NOCICEPTIVE PAIN

This application relies on the priority of provisional application Ser. No. 60/059,048(filed on Sep. 16, 1997).

FIELD OF THE INVENTION

The present invention is directed to the treatment of nociceptive pain in larger mammals, in particular humans, and to pharmaceutical analgesic formulations.

BACKGROUND OF THE INVENTION

There are a variety of analgesic agents available for pain treatment. The most potent analgesic agents are morphine and related opioid compounds. Since the compounds have the severe drawback of leading to dependence and addiction, other non-opioid analgesic compounds have been developed. Yet so far, all available analgesics possess undesirable side effects, which become particularly apparent upon long term use.

It is an object of the invention to develop new analgesic pharmaceutical preparations suitable for the treatment and/or prophylaxis of nociceptive pain in larger mammals, in particular in humans, with an improved activity profile and a favorable therapeutic ratio between antinociceptive activities and other side effects.

SUMMARY OF THE INVENTION

The present invention is directed to the use of 4-chloro-5-[(4,5-dihydro-1H-imidazol-2-yl)-amino]-6-methoxy-2-methylpyrimidine (generic name: moxonidine) and its physiologically compatible acid-addition salts for the treatment and/or prophylaxis of nociceptive pain, in larger mammals, in particular in humans, and for the manufacture of medicinal products suitable for this treatment and/or prophylaxis of nociceptive pain.

DETAILED DESCRIPTION OF THE INVENTION

Figure 1:
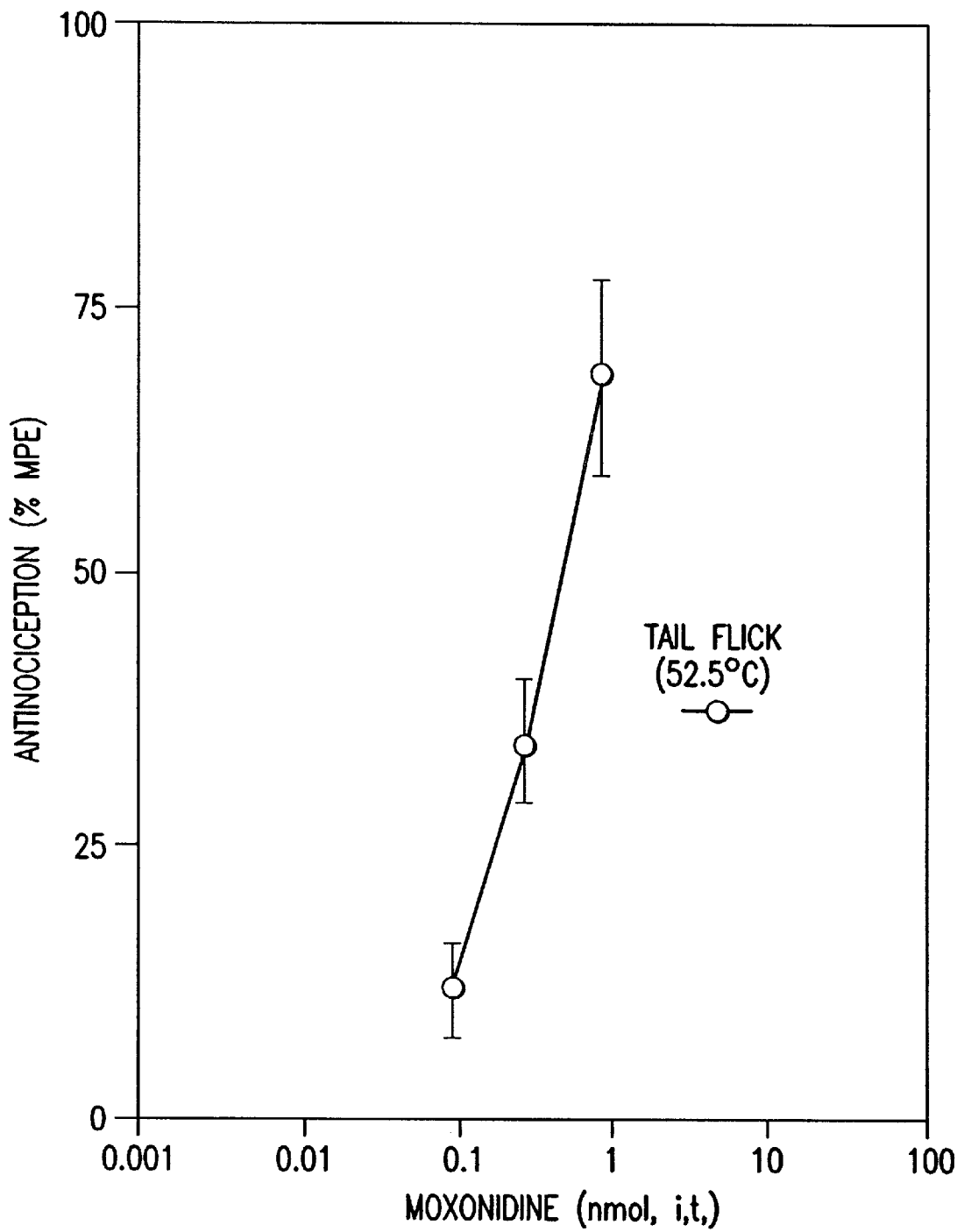
FIG. 1 shows dose-response curves for moxonidine-induced antinoception in ICR mice in the warm water immersion tail flick assay.

According to the invention, 4-chloro-5-[(4,5-dihydro-1H-imidazol-2-yl)-amino]-6-methoxy-2-methylpyrimidine of formula I

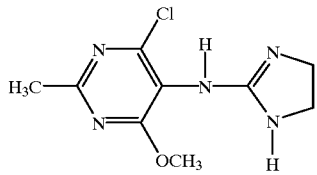

and its physiologically compatible acid-addition salts are used for the treatment and/or prophylaxis of nociceptive pain, i.e. nociceptive acute and chronic pain.

Salts with inorganic acids, such as hydrohalic acids, or with organic acids, for example lower aliphatic monocarboxylic or dicarboxylic acids such as acetic acid, fumaric acid or tartaric acid or aromatic carboxylic acids such as salicylic acid are suitable as physiologically compatible acid-addition salts of moxonidine.

The compounds used in accordance with the invention are within the scope of the 5-[(2-imidazolin-2-yl)-amino]-pyrimidine derivatives with blood pressure lowering properties described in the published German Patent Application No. 28 49 537, and are known from this patent application. Pharmaceutical preparations containing moxonidine are commercially available as antihypertensive medications under the trade name Physiotens . It is known that moxonidine is an imidazoline and $a_2$-adrenergic receptor agonist ($I_1/\alpha_2$-AR). The compounds can be manufactured in a known manner essentially in accordance with the processes described in the aforementioned published German Patent Application or in a manner similar to these processes.

It has now surprisingly been found that moxonidine and its physiologically compatible acid-addition salts provide for antinociception in larger mammals, in particular in humans, and are suitable for the treatment and/or prophylaxis of nociceptive pain, i.e. nociceptive acute and chronic pain.

The term "antinociception" means abatement or inhibition of acute or chronic nociceptive pain. Nociceptive pain includes all forms of somatic pain which result from damage or dysfunction of non-neural tissue. Acute nociceptive pain includes pain resulting from tissue-damaging stimulation such as that produced by injury or disease. Examples include postoperative pain, post traumatic pain, acute pancreatis, labor pain, muscle pain and pain accompanying myocardial infarction. Chronic nociceptive pain includes inflammatory pain, arthritis pain, cancer pain and other forms of persistent pain deriving from damaged or inflamed somatic tissue.

Moxonidine was tested for potential antinociceptive action in the tail flick thermal nociceptive test and the substance P (SP) nociceptive behavioral test in ICR mice, B6,129 mice and in mutant mice with a dysfunctional $\alpha_{2a}$ receptor. These experiments revealed that moxonidine produces antinociception in both strains of mice and in the dysfunctional $\alpha_{2a}$ mutant mice (designated "mutated mice") in both tests of antinociception. In order to further elucidate the antinociceptive action of moxonidine, the ability of the $\alpha_2$ AR-selective antagonist yohimbine to inhibit moxonidine-induced antinociception in the three strains of mice was also tested.

For the treatment and/or prophylaxis of nociceptive pain, i.e. nociceptive acute and chronic pain, with moxonidine and its physiologically compatible acid-addition salts in accordance with the invention, any suitable route of administration may be employed, i.e. the compound can be administered orally, intravenously, intrathecally or transdermally in conventional pharmaceutical preparations.

For example, according to the invention the antinociceptive quantities of the compounds that are used for the treatment and/or prophylaxis of nociceptive pain can be contained together with customary pharmaceutical excipients and/or additives in solid or liquid pharmaceutical formulations. Examples of solid dosage forms are tablets, coated tablets, capsules, powders, granules or suppositories. These solid dosage forms can contain standard pharmaceutical inorganic and/or organic excipients such as lactose, talc or starch in addition to customary pharmaceutical additives such as lubricants or tablet disintegrants. Liquid preparations such as solutions (i.e. solutions to be administered intrathecally) suspensions or emulsions of the active ingredients can contain the usual diluents such as water, oil and/or suspending aids such as polyethylene glycols and the like. Further additives such as preservatives and the like may also be added.

The active ingredients can be mixed and formulated with the pharmaceutical excipients and/or additives in a known manner. For the manufacture of solid dosage forms, for example, the active ingredients may be mixed with the excipients and/or additives in the usual manner and granulated in a wet or dry process. Granules or powder can be filled directly into capsules or compressed into tablet cores. If desired, these can be coated in a known manner. For the manufacture of liquid dosage forms the active compounds are dissolved in a suitable liquid carrier and optionally suitable adjuvants may be added.

Pharmaceutical compositions suitable for injection (i.e. for spinal intrathecal administration) may be sterilised solutions containing an antinociceptive amount of moxonidine dissolved in a physiologically acceptable isotonic saline solution (i.e., containing 0.9% by wt. sodium chloride). Usually these solutions are adopted in a known manner to the physiological characteristics of the site of administration.

Test and Results

The antinociceptive activity of moxonidine can be demonstrated in pharmacological standard tests in mice, e.g. in the tail flick test and the substance P (SP) nociceptive test.

The following experiments demonstrate that intrathecally administered moxonidine produces antinociception in mice. Antinociception was detected via the hot water (52.5° C.) tail flick test and the intrathecal substance P (SP) nociceptive test. Moxonidine was intrathecally administered to ICR mice, B6,129 mice or to mutated mice. The $\alpha_2$ AR-selective antagonist yohimbine was tested for inhibition of moxonidine-induced antinociception. Moxonidine prolonged tail flick latencies with $ED_{50}$ values of 0.5 nmol (0.3–0.7) in ICR, 0.17 nmol (0.09–0.32) in B6,129 mice and 0.32 nmol (0.074–1.6) in mutated mice. Moxonidine inhibited SP-elicited behavior with $ED_{50}$ values of 0.04 nmol (0.03–0.07) in ICR, 0.4 nmol (0.3–0.5) in B6,129 mice, and 1.1 nmol (0.7–1.7) in mutated mice. Yohimbine attenuated moxonidine-induced antinociception in all strains of mice. Yohimbine antagonism of moxonidine-induced antinociception implicates the participation of $\alpha_2$ ARs in an antinociceptive activity of moxonidine. The moxonidine potencies of B6,129 mice and mutated mice are of the same order. This suggests that receptors other than $\alpha_{2a}$ are required for moxonidine-induced antinociception. The results of additionally carried out $\alpha_{2c}$ antisense pretreatments in ICR mice followed by moxonidine treatment and assay for moxonidine-induced antinociception in the SP nociceptive test point to the same conclusion.

List of Abbreviations:

AR: adrenergic receptors; $ED_{50}$ value: effective dose 50%; $ED_{80}$ value: effective dose 80%; $ID_{50}$: inhibitory dose 50% value; $I_1$: imidazoline$_1$; i.p.: intraperitoneal; i.t.: intrathecal; % MPE: percent maximum possible effect; μg: microgram; ng: nanogram; nmol: nanomoles; pmol: picomoles; SP: substance P; S.D.: standard deviation; S.E.M.: standard error of the mean.

Animals:

Experimental subjects were 20–25 g male ICR mice (Harlan Sprague Dawley, Madison, Wis.) or 15–20 g male and female mice (gender-matched) with a C57BL/6 and 129/sv genetic background (designated B6,129). Also used were mutated mice ($\alpha_{2a}$-dysfunctional). Subjects were housed in groups of five to ten in a temperature- and humidity-controlled environment. Subjects were maintained on a 12 hr light/dark cycle and had free access to food and water.

Chemicals:

Moxonidine (4-chloro-5-[(4,5-dihydro-1H-imidazol-2-yl)-amino]-6-methoxy-2-methylpyrimidine) in the form of the hydrochloride (Solvay Pharma GmbH, Hannover, Germany) was dissolved in an aqueous 1% by vol. acetic acid solution and diluted with acidified saline solution (pH 3.2–4.0). Substance P and yohimbine (17 α-hydroxy-yohimban-16α-carboxylic acid methyl ester)(Sigma, St. Louis, Mo.) were dissolved in acidified saline solution. All drugs were administered intrathecally in a 5 μl volume in conscious mice. Antisense and mismatch oligonucleotides to the $\alpha_{2c}$ receptor of mice were obtained from the Midland Certified Reagent Co. (Midland, Tex.).

Thermal Nociception Tail Flick Test Procedure:

Thermal nociceptive responsiveness was determined using the traditional warm water (52.5° C.) immersion tail flick test. The latency to the first rapid tail flick represented the behavioral endpoint. Baseline measurements of tail-flick latencies were collected on all mice prior to testing. The mean baseline tail flick latency of the ICR mice was 3.6 seconds (S.D.: 0.69 s, n=31); ICR mice that failed to respond within 5 seconds to baseline tests were excluded from analysis. The mean baseline tail flick latency of the B6,129 mice and mutated mice was 6.4 seconds (S.D.: 2.6 s, n=250); the baseline tail flick latency did not differ (unpaired t test: p>0.05) between the B6,129 mice and mutated mice (B6, 129: mean=6.5 s, S.D.=2.5 s, S.E.M.=0.27 s, n=133 mice; mutated mice: mean 6.2 s, S.D.=2.7 s, S.E.M.=0.24 s, n=85 mice). B6,129 mice and mutant mice that failed to respond within 11.5 seconds (a value greater than 2 standard deviations from the mean) were eliminated from analysis (5.5%) The percent of maximum possible antinociceptive effects (% MPE) of injected drug- or saline control-solutions were determined according to the following formula:

$$\% \, MPE = \frac{\text{Post-drug Latency} - \text{Pre-drug Latency}}{\text{Cutoff} - \text{Pre-drug Latency}} \times 100$$

In all three lines of mice, a maximum score of 100% was assigned to those animals not responding before a 12 second cutoff in order to avoid tissue injury. In each case where the animal did not respond before the 12 second cutoff, the tail was examined for loss of motor control. Only those animals capable of movement in their tails were included in analysis.

The $ED_{50}$ was calculated as the dose that produces a 50% increase of the tail flick latency.

Substance P Nociceptive Test Procedure:

Nociceptive responsiveness was also tested in the substance P-induced nociceptive test. This SP assay is a sensitive indicator of milder analgesics. A constant dose of SP (15 ng for ICR mice; 10 ng for B6,129 mice and mutated mice)

was injected intrathecally in order to produce baseline behaviours of approximately 40–60 behaviours (scratches and bites directed to the hindlimbs) per minute. Intrathecal co-administration of an antinociceptively active test compound dose-dependently inhibits those behaviours. To test the ability of the agents to inhibit SP-induced behaviour, the drugs were co-administered with SP and % inhibition of SP-induced behavior was calculated according to the following equation:

$$\% \text{ Inhibition} = \frac{\text{Control} - \text{Experimental}}{\text{Control}} \times 100$$

The ability of moxonidine to inhibit SP-induced behaviour was also tested when given by a systemic route of administration (intraperitoneal). In this case, moxonidine was given as a 1 hour pretreatment and SP was then administered intrathecally.

The $ED_{50}$ value was calculated as the dose that produces a 50% reduction of SP induced behavioral responses per minute.

Antagonism of Moxonidine Effects by an $\alpha_2$ Adrenergic Antagonist:

In some experiments, yohimbine was co-administered with the moxonidine-SP combinations.

Yohimbine Antagonism in Tail Flick Test.

ICR mice were co-administered yohimbine (3 nmol, i.t.) and a high efficacy dose of moxonidine (2 nmol, i.t.) in the tail flick test.

Yohimbine Antagonism in Substance P Test.

ICR and B6,129 mice were co-administered yohimbine (0.1 nmol, i.t.) and a high efficacy dose of moxonidine (0.3 nmol, i.t.) in the substance P nociceptive test. Mutated mice were co-administered yohimbine (0.1, 2.5 nmol, i.t.) and a high efficacy dose of moxonidine (6 nmol, i.t.) in the substance P nociceptive test.

Behavioral Testing after Alpha2C Antisense Oligonucleotide Pretreatment:

Experimental subjects were 20–25 g male ICR mice. Animals were housed in a temperature- and humidity-controlled environment. Antisense (5'-CCA-TTC-GCC-CGC-GTC-GCT-CC-3') and mismatch (5'-GCA-TGC-GCC-CTC-GTC-CCT-CC-3') oligonucleotides to the $\alpha_{2c}$ receptor were reconstituted in sterile saline solutin at a final concentration of 2.5 mg/ml. The resulting oligonucleotide solutions were injected intrathecally by direct lumbar puncture with a volume of 5 $\mu$l (12.5 $\mu$g) per injection. The injections were given on a twice daily schedule (08:00 and 20:00 hr) for three days prior to testing. Three groups of mice (n>8/group) were given the following treatments in each study: an antisense oligonucleotide, a mismatch oligonucleotide, or a vehicle. On day 4 after treatment the animals were assayed for moxonidine-induced antinociception using the substance P nociceptive test.

Statistical Analysis.

Data describing antinociception are expressed as means of percent maximal possible effect (% MPE) or percent inhibition (% inhibition) with standard error of the mean (S.E.M.). In experiments where full dose-response curves were generated, a minimum of three doses were used for each drug or combination of drugs. Potency differences are presented as dose ratios between the $ED_{50}$ values (the dose calculated to produce 50% MPE) of different dose-response curves. Statistical comparisons of potencies are based on the confidence limits of the $ED_{50}$ values. A shift in a dose-response curve is considered significant when the calculated $ED_{50}$ value of one curve falls outside the confidence limits of the $ED_{50}$ value of the curve to which it is being compared.

The $ED_{50}$ values and confidence limits were calculated according to the method of Tallarida and Murray. In the experiments that tested for yohimbine antagonism of a single dose of moxonidine the statistical significance was evaluated using Student's t test (significance set at p<0.05). Groups of 7 or greater animals were used for each dose.

Figure 2:
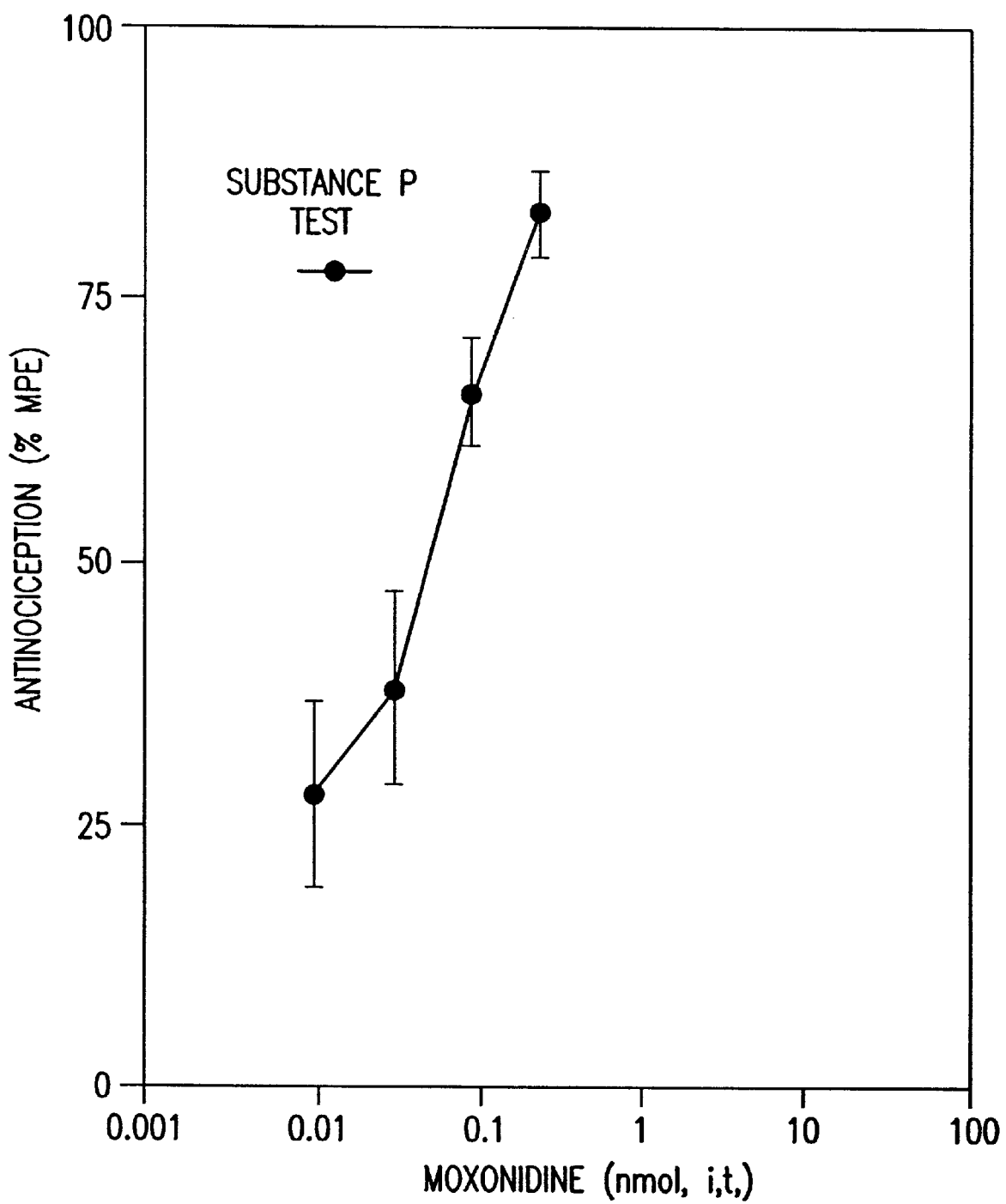
FIG. 2 shows dose-response curves for moxonidine-induced antinoception in ICR mice in the SP nociceptive behavioral assay.
Figure 3:
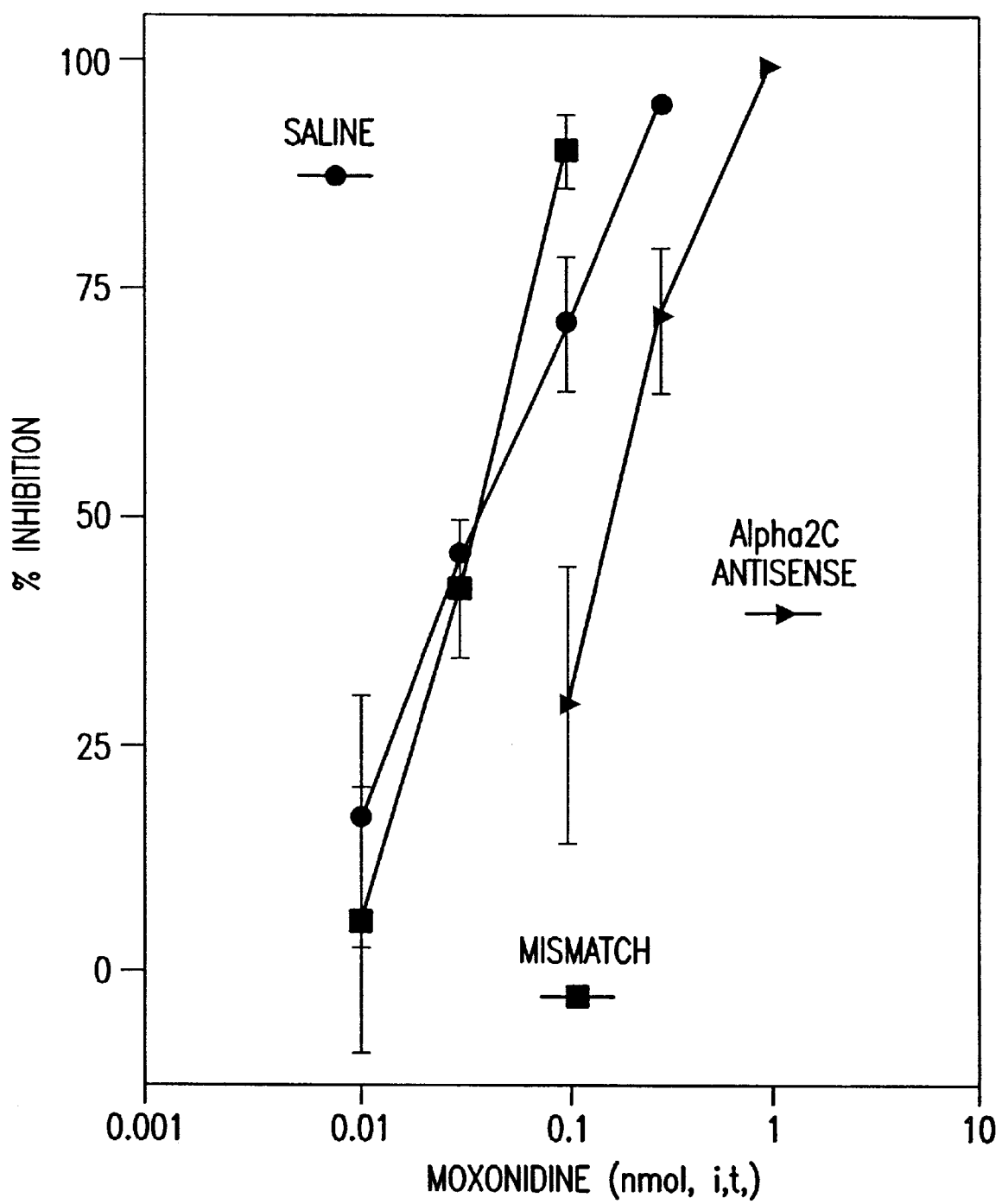
FIG. 3 shows dose-response curves for moxonidine-induced antinoception after $\alpha_{2c}$ antisense oligonucleotide pretreatment in ICR mice in the SP nociceptive behavioral assay.

FIG. 1 shows dose-response curves to intrathecally administered moxonidine in ICR mice in the warm water immersion tail flick assay ($ED_{50}$: 0.04 nmol (0.03–0.07); open circles). The curves demonstrate that the moxonidine produced spinal antinociception. FIG. 2 shows dose-response curves to intrathecally administered moxonidine in ICR mice in the SP nociceptive behavioral assay ($ED_{50}$: 0.5 nmol (0.3–0.7) closed circles). The curves demonstrate that the moxonidine produced spinal antinociception. FIG. 3 shows dose-response curves to intrathecally administered moxonidine in ICR mice in the SP nociceptive behavioral assay after $\alpha_{2c}$ antisense oligonucleotide pretreatment (saline, $ED_{50}$: 0.03 nmol (0.019–0.045); mismatch, $ED_{50}$: 0.034 (0.024–0.047); $\alpha_{2c}$ antisense, $ED_{50}$: 0.17 (0.11–0.26).

Moxonidine-Induced Antinociception

Moxonidine produces antinociception in ICR mice in the tail flick nociceptive test. Dose-response curves (FIG. 1 and FIG. 2) were determined for the effects of moxonidine (0.1, 0.3, 1, nmol, i.t.) in the tail flick test in ICR (0.1, 0.3, 1 nmol, i.t; $ED_{50}$ value: 0.5 (0.3–0.7) and in the SP (15 ng) nociceptive behavioral test in (doses: 0.01, 0.03, 0.1, 0.3 nmol, i.t.; $ED_{50}$ value: 0.04 (0.03–0.07)). The lower $ED_{50}$ value of moxonidine in the SP test versus the tail flick test is consistent with comparisons made between the tests for other antinociceptive compounds.

Antagonism of Moxonidine-Induced Antinociception

To test for participation in the mechanisms governing moxonidine-induced antinociception, the $\alpha_2$ AR-selective antagonist yohimbine was co-administered with moxonidine in ICR mice in the tail flick test and the substance P test. Yohimbine (2.5 nmol, i.t.) effectively antagonized moxonidine-induced antinociception in the tail flick test in ICR mice. Yohimbine (0.3 nmol, i.t.) effectively antagonized moxonidine-induced inhibition of substance P behaviour in ICR mice.

The abilities of yohimbine to antagonize the antinociceptive effect of moxonidine in ICR mice strongly suggested the participation of an $\alpha_2$ AR in moxonidine-induced antinociception. It was suggested in the literature that the $\alpha_{2a}$ AR subtype is the primary mediator of $\alpha_2$ AR agonist-mediated antinociception. To examine the participation of the $\alpha_{2a}$ AR subtype in moxonidine-mediated antinociception, moxonidine was tested for its ability to inhibit both the tail flick response and SP-elicited behaviour in mice with a mutation in the $\alpha_{2a}$ AR.

Tests were also carried out for moxonidine-induced antinociception in the B6,129 mice. Moxonidine dose-dependently (0.01, 0.03, 0.1, 0.3, 10 nmol, i.t. $ED_{50}$ value: 0.17 nmol (0.89–1.32)) produced potent antinociception in B6,129 mice in the tail flick test. Furhermore, we tested moxonidine for the ability to inhibit SP-induced scratching and biting behaviour. Moxonidine (0.1, 0.3, 1 nmol, i.t.; $ED_{50}$ value: 0.4 nmol (0.3–0.5); and 3, 10, 30 mg/mouse, i.p.; $ED_{50}$ value: 12 mg (10–15)) dose-dependently inhibited the SP-induced nociceptive behaviour.

The dose-response curves for moxonidine antinociception in mutated mice in the tail flick test (0.01, 0.1, 1, 3 nmol, $ED_{50}$ value: 0.32 (0.074–1.6)) and in the substance P nociceptive test (0.1, 1, 10 nmol, $ED_{50}$ value: 1.1(0.7–1.7)) were then determined. In both tests, moxonidine potency was approximately 2-fold lower in the muted mice than in the B6,129 mice.

Moxonidine produced potent antinociception in the tail flick test and the substance P nociceptive test in two different strains of mice (ICR; B6,129). Moxonidine-induced antinociception was antagonized by yohimbine. Moxonidine potency was decreased merely two-fold in the mutated mice compared to the B6,129 mice. Taken together, those data suggest that moxonidine-induced antinociception is governed by some $\alpha_2$ AR subtype, but not likely the $\alpha_{2a}$ AR subtype.

Antisense Oligonucleotide Treatment and Behavioral Testing:

Moxonidine potency is reduced in animals that are "knocked-down" for the $\alpha_{2C}$ adrenergic receptor subtype through antisense oligonucleotide administration. Thus, moxonidine inhibited SP-elicited behavior in mice pretreated with saline solution ($ED_{50}$ value: 0.03 nmol (0.019–0.045), circles), mismatch sequence containing solution ($ED_{50}$ value: 0.034 nmol (0.024–0.047), squares), and $\alpha_{2C}$ AR antisense oligonucleotide containing solution ($ED_{50}$ value: 0.17 nmol (0.11–0.26), rightward triangles). For further elucidation the data are represented in FIG. 3 showing a dose-response curve derived from the results of the $\alpha_{2c}$ antisense experiments in mice.

The experimental results from the $\alpha_{2c}$ antisense experiments show that moxonidine-induced antinociception in mismatch oligonucleotide-treated mice did not differ from that of saline-treated mice. However, pretreatment of mice with $\alpha_{2C}$ AR antisense oligonucleotide resulted in a 6-fold rightward shift in the moxonidine dose-response curve relative to that of saline- or mismatch-pretreatment. Thus, the results from the the $\alpha_{2c}$ antisense oligonucleotide experiments suggest that moxonidine-induced antinociception may require participation by the $\alpha_{2c}$ AR subtype.

The results of the foregoing experiments are a clear indication that antinoception is provided after administration of moxonidine.

Moxonidine and its acid-addition salts are therefore suitable for the treatment and/or prophylaxis of nociceptive pain in nociceptive acute and chronic pain conditions. The doses to be administered may differ between individuals and naturally vary depending on the type of condition to be treated and the route of administration. For example, locally applicable formulations, in particular intrathecally injectable formulations, generally contain substantially less amount of active substance than systemically applicable formulations. For example, solutions containing 10 to 100 μg per single unit dosage are suitable for intrathecal injections. Continuous application may be needed for chronic pain conditions.

The following example is intended as a more detailed illustration of the manufacture of a pharmaceutical preparation containing moxonidine that is suitable for the treatment and/or prophylaxis of nociceptive pain in humans, however, without limiting the scope of the application.

EXAMPLE 1

Liquid preparation containing moxonidine for intrathecal administration comprises:
Moxonidine hydrochloride: 15 mg
Isotonic aqueous saline solution: quantum satis ad 1 l
Moxonidine was dissolved in the saline solution. The resulting solution was filled into ampoules of 1 ml content and sterilised.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Method of inhibiting nociceptive pain in mammals, comprising administering to a mammal a composition comprising an antinociceptively effective amount of the compound of formula I,

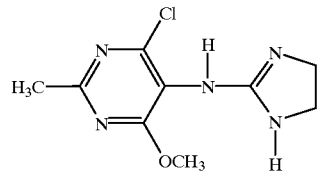

or a pharmaceutically acceptable acid-addition salt thereof.

2. A method of inhibiting nociceptive pain in mammals, comprising administering to a mammal a composition comprising an antinociceptively effective amount of the compound of formula I,

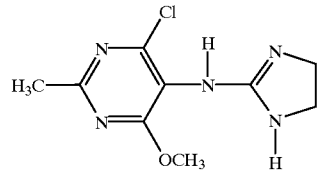

or a pharmaceutically acceptable acid-addition salt thereof, wherein said administering is intrathecally.

3. A method of inhibiting nociceptive pain in mammals, comprising administering to a mammal a composition comprising an antinociceptively effective amount of the compound of formula I,

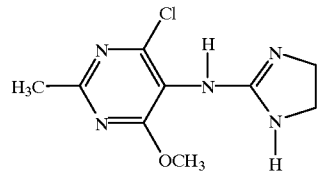

or a pharmaceutically acceptable acid-addition salt thereof, wherein said administering is systemically.

* * * * *